United States Patent [19]
Fernandez et al.

[11] Patent Number: 5,180,860
[45] Date of Patent: Jan. 19, 1993

[54] DEHYDROHALOGENATION PROCESS

[75] Inventors: Richard E. Fernandez, Bear; Ralph B. Kaplan, Wilmington, both of Del.

[73] Assignee: E. I. Du Pont de Nemours and Company, Wilmington, Del.

[21] Appl. No.: 545,246

[22] Filed: Jun. 28, 1990

[51] Int. Cl.$^5$ .............................................. C07C 17/34
[52] U.S. Cl. ................................... 570/157; 570/155
[58] Field of Search ....................... 570/157, 228, 155

[56] References Cited

U.S. PATENT DOCUMENTS

T922,005 5/1974 Briggs .................................. 570/228
3,361,786 1/1968 Fink .................................... 570/228

Primary Examiner—Alan Siegel
Attorney, Agent, or Firm—H. M. Wolfson

[57] ABSTRACT

A process for the dehydrohalogenation of saturated hydrogen-containing polyhalocarbons using liquid alkali metal acid fluoride and/or alkali metal fluoride compositions to form haloolefins.

7 Claims, No Drawings

DEHYDROHALOGENATION PROCESS

FIELD OF THE INVENTION

This invention relates to the dehydrohalogenation of saturated hydrogen-containing polyhalocarbons with liquid alkali metal acid fluoride and/or fluoride compositions. More specifically, it relates to a process wherein a saturated hydrogen-containing polyhalocarbon, having two or more carbon atoms, bearing a halogen (preferably chlorine) substituent on a carbon atom adjacent to a carbon atom bearing a hydrogen substituent, is converted to a haloolefin having at least one halogen substituent on an unsaturated carbon atom.

PRIOR ART

Haloolefins having one or more halogen substituents attached to an unsaturated carbon atom are valuable intermediates for producing hydrogen-containing fluorinated hydrocarbons by the reaction of the haloolefin with HF generally in the presence of a catalyst, and as monomers, for the production of polymers.

Hydrogen-containing fluorocarbons are desirable for their low ozone depletion potentials, notable are $CF_3CH_2Cl$(HCFC-133a) intermediate to $CF_3CH_2F$(HFC-134a), $CF_3CH_2F$(HFC-134a), $CH_3CClF_2$(HCFC-142b), $CF_3CHF_2$(HFC-152a), $CF_3CHCl_2$(HCFC-123) and $CF_3CHClF$(HCFC-124). Such compounds are potential candidates to replace certain commercially employed perhalocarbons suspected of contributing to the destruction of stratospheric ozone.

The art describes various processes for preparing hydrogen-containing fluorocarbons. One such method involves liquid phase halogen exchange between a saturated halocarbon precursor of the desired fluorohydrocarbon and a metal fluoride, such as an antimony pentachlorofluoride or pentafluoride with or without HF present to maintain the fluoride content of the metal fluoride. The hydrogen-containing product of the liquid phase reaction is sometimes accompanied by unwanted perhalocarbons or carbon-carbon cleavage products of ethanes and higher carbon content material, particularly where high fluorine content metal fluoride reactants are required for the production of high fluoride content halohydrocarbons.

Vapor phase halogen exchange processes, on the other hand, generally require large excesses of HF, and therefore, suffer from the need to employ expensive high pressure equipment to contain such volatile reactants in the reaction zone and for recycling the excess to the reactor.

HF-addition to unsaturated precursors of the desired fluorohydrocarbons is attractive because it does not normally require large HF excesses and can provide the saturated addition products in high yields and substantially free of perhalogenated and carbon-carbon cleavage by-products.

Copending patent application Ser. No. 07/480,605 describes a process for the halogen exchange production of hydrogen-containing saturated fluorocarbons based on the use of substantially molten alkali metal acid fluorides. Such processes are sometimes accompanied by unsaturated by-products. The present invention is designed to provide a process for the production of unsaturated halocarbons suitable for the production of hydrogen-containing saturated fluorocarbons by HF-addition or halogen-addition by any method known to the art or suitable for use as monomers for the production of polymeric derivatives.

Copending patent application Ser. No. (CH-1764) relates to a novel HF-addition process for converting the unsaturated by-products to hydrogen-containing saturated fluorocarbons involving alkali metal acid fluorides as the source of HF.

SUMMARY OF THE INVENTION

The present invention involves a process for preparing haloolefins containing at least one halogen substituent attached to an unsaturated carbon atom, which process comprises the following steps:

(1) contacting component A, a halohydrocarbon having a hydrogen substituent and a halogen substituent on adjacent saturated carbon atoms and at least one other halogen substituent on at least one of the adjacent saturated carbon atoms with component B, an anhydrous substantially liquid reaction medium containing at least one of an alkali metal acid fluoride and an alkali metal fluoride, to form a reaction mixture.

(2) maintaining the reaction mixture at a temperature and pressure and for a time sufficient to form at least one haloolefin having at least one halogen substituent attached to an unsaturated carbon atom, and (3) recovering at least one haloolefin from the reaction mixture.

Preferably, the substantially liquid reaction medium is a substantially molten alkali metal acid fluoride or a mixture thereof with an alkali metal fluoride. The halogen substituent on the carbon adjacent to the hydrogen-bearing carbon atom is preferably a non-fluorine halogen, usually chlorine. It is also preferred that at least one halogen attached to an unsaturated carbon atom is chlorine or fluorine, usually fluorine.

DETAILED DESCRIPTION

In general, the process is conducted by intimately contacting, batchwise or continuously, a dehydrohalogenatable halohydrocarbon with a substantially liquid dehalogenating medium as defined, under vigorous agitation, at an effective temperature and pressure and for a time sufficient and effective to result in the formation of at least one haloolefin; separating the reaction products from the liquid dehydrohalogenating medium and recovering the haloolefin(s) from the reaction products. The reaction products may also contain fluorinated halogen exchange products as well as the desired haloolefins. The organic reaction product can be separated from the liquid reaction medium and the haloolefin(s) recovered therefrom by any means known to the art, usually and conveniently by distillation. The liquid reaction medium containing alkali metal acid fluoride and/or alkali metal fluoride can be a molten salt composition consisting essentially of the acid fluoride with or without alkali metal fluoride. The alkali metal acid fluorides are preferred and may contain alkali metal fluorides as described below.

It is believed fluoride ion is the most active dehydrohalogenating agent present in the liquid media of the present invention. Fluoride ion can be generated in situ from acid fluoride ion by dissociation, as illustrated in the following equation with alkali metal bifluoride, $MHF_2$, and alkali metal fluoride, MF.

$$MHF_2 \rightarrow MF + HF$$

$$MF \rightarrow M^+ + F^-$$

Alternatively, fluoride ion can be provided as free alkali metal fluoride with the carrier solvent being a molten alkali metal acid fluoride and in sufficient quantity to provide a substantially liquid reaction medium.

The alkali metal fluorides and acid fluorides are well-known compositions. The acid fluorides are conventionally prepared by reaction of an alkali metal chloride or fluoride with hydrogen fluoride. When molten, the acid fluorides exist largely as alkali metal cations, $M^+$, and acid fluoride anions, $[H_nF_{n+1}]^-$, where "n" is at least 1, depending upon the number of molecules HF associated with the fluoride ion. It is convenient, however, to represent them as $MF \cdot nHF$, where M is the alkali metal and "n" is at least 1. For purposes of this invention, that is, to effect dehydrohalogenation of suitable halohydrocarbons, "n" is preferably not greater than about 1.5, more preferably not greater than about 1.1, most preferably about 1.

The molten salt composition will preferably be so constituted as to form a melt without decomposition below about 240° C., more preferably below about 225° C. Melting characteristics of alkali metal acid fluorides, $MF \cdot nHF$, where $n=1$ and 2 are tabulated below. It can be seen that melting point is a function of both the alkali metal cation, "M" and the number, "n".

| Melting Points (°C.) of Alkali Metal Acid Fluorides MF.nHF | | |
|---|---|---|
| Metal, M | n = 1 | n = 2 |
| Li | * | — |
| Na | ** | — |
| K | 226(3), 238(4) 239(5), 236(6) | approx. 72 |
| Rb | 204(3), 210(4) 205(5) | approx. 52 |
| Cs | 180(4), 176(5) | approx. 30 |

*decomposes at 200 without melting
**decomposes at 278 without melting
(3) Chandhuri et al., Chem. Ind. (London) 88 (1979)
(4) Westrum et al., J. Chem. Thermodyn. 10,835 (1970)
(5) Winsor et al., J. Amer. Chem. Soc., 70,1500 (1948)
(6) Opalovski et al., J. Thermal Anal., 2, 373 (1970)

The lower the melting point the more fluid the composition and the more useful it is for the present purpose. For this reason, the alkali metal of the acid fluoride will normally be K, Rb or Cs, preferably Rb or Cs.

Molten salt compositions containing both alkali metal fluoride as well as alkali metal acid fluoride are preferred. Such compositions yield the best dehydrohalogenation results by providing "free" fluoride ion as the dehydrohalogenating agent. Any of the alkali metal fluorides may be used to provide the "free" fluoride ion source when used in mixtures with any one or more of the alkali metal bifluorides (n=1) provided the bifluoride-fluoride mixtures are substantially molten at the operating temperature. Preferred are the K, Rb and Cs fluorides. The "free" fluoride content is generally in the range of about 0.05 to 1 mole per mole of bifluoride, preferably 0.1 to 0.5. Cesium bifluoride and cesium fluoride, for example, form a eutectic consisting of about 54 mole % bifluoride and 46% fluoride melting at about 152° C. Practically speaking, the existence of "free" fluoride in mixed acid-fluoride salts depends upon the presence of bifluoride since any higher acid fluoride will consume fluoride per the following equation.

$$H_2F_3^- + F^- = 2HF_2^-$$

By "substantially molten" is meant that the dehydrohalogenating medium may contain insolubles, such as by-product metal halides, so long as the liquid phase contains alkali metal acid fluorides with and without metal fluoride and is stirrable at the operating temperature.

The molten salt composition may also include minor amounts, e.g., up to 50% by weight of the composition, of fluorides of other metals, such as the alkaline earth metals, aluminum and others that are compatible to the extent that they do not interfere with the dehydrohalogenation reaction and the resulting mixed salt composition has the desired melting characteristics.

As the dehydrohalogenation reaction between the halohydrocarbon and the alkali metal acid fluoride, with or without alkali metal fluoride, proceeds, it can become enriched in nonfluorine halide ion as shown below.

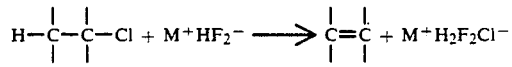

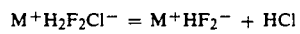

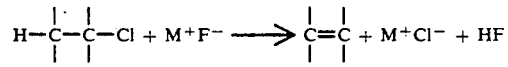

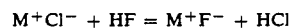

The nonfluorine halide, as HX, can be removed from the reaction mixture, if desired, by distillation or entrainment with an inert carrier gas.

Thus, it will be apparent that the subject alkali metal acid fluorides and fluorides can be produced from the corresponding alkali metal nonfluoride (the chloride) by treatment with anhydrous HF with the elimination of the by-product hydrogen halide, (HCl), from the mixture.

Further, the desired hydrogen halide level in the alkali metal acid fluoride as well as that of the free fluoride level (as alkali metal fluoride) in the molten alkali metal acid fluoride-based dehydrohalogenation system can be maintained by the addition of alkali metal fluoride—intermittently or continuously—during the course of the reaction.

The quantity of the alkali metal fluoride source, including the acid fluoride as the fluoride source, may vary widely. Preferably, at least a molar equivalent of fluoride, taken as the sum of MF and MF·HF, when both are present, is employed. An excess of such fluoride with not more than about 10 molar proportions is normally required.

Progress of the reaction can be followed by sampling the organic component of the reaction mixture. As stated above, additional alkali metal fluoride and/or acid fluoride (preferably bifluoride) can be added as needed during the course of the reaction to maintain a desired level of fluoride in the reaction mixture as well as to keep the reaction mixture substantially molten and stirrable.

The process is applicable to saturated halohydrocarbons, i.e., composed of carbon, hydrogen and halogen, having two or more carbon atoms, a hydrogen substituent on one carbon atom, at least one halogen substituent, preferably nonfluorine, on an adjacent carbon atom, and at least one halogen substituent attached to one or more of the two adjacent saturated carbon atoms. The halohydrocarbons will normally contain 2 to 6 carbon atoms, preferably 2 to 3 carbon atoms, and 2 or more halogen atoms, preferably 2 to 6 halogen atoms, preferable with at least one nonfluorine substituent present on the carbon atom adjacent to the hydrogen-bearing carbon atom.

The nonfluorine substituent present on the carbon adjacent to the hydrogen-bearing carbon atom is preferably chlorine. The "at least one halogen substituent on one or more of the two adjacent saturated carbon atoms" is preferably chlorine or fluorine, more preferably fluorine. The haloolefin also preferably contains 2 to 3 carbon atoms, and 2 or more halogen substituents, which are usually chlorine and/or fluorine substituents. Preferred halohydrocarbons contain 2 to 3 carbon atoms. Representative and typical dehydrohalogenatable halocarbons along with representative haloolefinic products are tabulated below.

| Representative Starting Materials | Representative Products |
|---|---|
| $CH_3CCl_3$ | $CH_2=CCl_2$ |
| $CH_3CHCl_2$ | $CH_2=CHCl$ |
| $CH_2ClCH_2Cl$ | $CHCl=CHCl$ |
| $CH_2ClCHClF$ | $CClF=CHCl$ |
| $CCl_2FCH_2Cl$ | $CF_2=CHCl$ |
| $CClF_2CH_2Cl$ | $CHCl=CCl_2$ |
| $CHCl_2CHCl_2$ | $CHF=CCl_2$ |
| $CHClFCHCl_2$ | $CHF=CClF$ |
| $CHF_2CHCl_2$ | $CHF=CHCl$ |
| $CHF_2CHClF$ | $CF_2=CHCl$ |
| $CH_3CCl_2F$ | $CF_2=CHF$ |
| $CH_3CClF_2$ | $CH_2=CClF$ |
| $CH_3CF_3$ | $CH_2=CF_2$ |
| $CH_2ClCF_3$ | $CF_3CF=CHCl$ |
| $CH_2ClCClF_2$ | |
| $CF_3CFClCH_2Cl$ | |

The process is conveniently conducted batchwise by mixing the reactants in a closed or ventible system and heating the mixture under agitation at a desired temperature and pressure. The pressure can be controlled with a pressure relief valve if desired. It can also be conducted continuously or semi-continuously with the saturated material to be dehalogenated fed to the reaction vessel containing the alkali metal composition which has also been fed continuously or semi-continuously. Since the dehydrohalogenated products are generally gaseous at the operating temperatures and pressures, it is convenient to bleed off a portion of the vapor phase intermittently or continuously during the course of the reaction.

The volatile portion of the reaction product mixture exiting the reactor contains the desired unsaturated material, unreacted saturated starting material, if any, and saturated fluorinated material, if any. The product mixture can be resolved into its components by any of a variety of well-known techniques, including aqueous washings to remove acid, followed by drying and fractional distillation. Unreacted saturated as well as any hydrogen-containing fluorinated products that are potentially dehydrohalogenable can be recycled to the reaction as desired.

The dehydrohalogenation temperature can vary widely provided it is sufficiently high to maintain the alkali metal dehydrohalogenating medium substantially liquid without causing the decomposition of the saturated halocarbon reactant or the unsaturated halocarbon product. The reaction temperature will normally range from about 150° to 500° C., depending upon the particular saturated halocarbon reactant, the unsaturated product(s) derived therefrom and the alkali metal composition employed. Preferably the temperature will range from about 200° to 450° C., more preferably 250° to 400° C.

Reaction pressure is not critical. It may vary from subatmospheric to superatmospheric. Preferably, it is at least atmospheric. Superatmospheric pressure, up to about 30 atmosphere may be used to the extent that the solubility of the organic reactant in the alkali metal dehydrohalogenation medium increases with pressure and results in increased reaction rate and/or conversion to the unsaturated product.

Reaction time may also vary depending upon the reactants employed and the result desired.

The reaction vessel should be constructed of materials resistant to the action of the reactants. Examples of suitable materials include stainless steels, high nickel alloys, such as "Hastelloy" and "Inconel" and plastics, such as polyethylene, polychlorotrifluoroethylene and polytetrafluoroethylene.

To illustrate the invention, the following examples were conducted in a 600 ml autoclave composed of stainless steel, "Inconel" alloy or "Hastelloy" C equipped with a stirrer. A heating mantle controlled by a thermocouple was centered within the autoclave. A pressure transducer for monitoring pressure was also within the autoclave along with a reaction effluent tube connected in series with a gas scrubber containing aqueous caustic and means for collecting and analyzing the reaction effluent. Analyses were conducted with the aid of gas chromatography (GC) alone or in conjunction with mass spectroscopy (MS).

EXAMPLE 1

To a "Hastelloy" C Parr autoclave (600 cc) was added 759.5 g (5.0 mole) CsF and 90 g (4.5 mole) HF. Pot composition approximated CsF·0.9HF. The autoclave was sealed and heated to 154° C. Then $CCl_2FCH_2Cl$(HCFC-131a) was pumped to the reactor at a rate of ca. 1.3 g/minute. The reactor was sampled constantly by passing the reactor effluent through a caustic scrubber and then a gas bulb. Thus, both liquid and gas samples were taken simultaneously. The reactor temperature, initially at 150° C., was raised after 25 minutes to 200° C. and then after an additional 25 minutes to 250° C. Eleven liquid samples and ten gas samples were collected over the 61 minute run time. Fifty-three percent of the feed was recovered as liquid samples, the remainder being non-condensed and represented in composition by the collected gas samples. The liquid samples consisted primarly of unreacted $CCl_2F_2CH_2Cl$ and $CHCl=CClF$ (via loss of HCl from $CCl_2FCH_2Cl$). The gas samples consisted predominatly of $CHCl=CClF$, $CF_2ClH_2Cl$, $CHCl=CF_2$ (via loss of HCl from $CF_2ClCH_2Cl$ or HF from $CF_3CH_2Cl$), $CF_3CH_2Cl$ and $CF_3CH_2F$.

The haloolefins $CHCl=CClF$(HCFC-1121) and $CHCl=CF_2$(HCFC-1122) can be converted, via HF-addition reactions, to $CH_2ClCClF_2$(HCFC-132b) and $CH_2ClCF_3$(HCFC-133), thence by halogen exchange to $CF_3CH_2F$(HFC-134a). They are also intermediates, via $Cl_2$ addition, to $CHCl_2CCl_2F$ and $CHCl_2CClF_2$, then by halogen exchange fluorination to $CHCl_2CF_3$(HCFC-123).

EXAMPLE 2

760 g (5 moles) CsF and 90 g (4.5 moles) HF were added to a "Hastelloy" C 600 ml autoclave to provide approx. 5 moles of CsF 0.9 HF. The reactor was heated with stirring to 250° C. and $CHClFCH_2Cl$(HCFC-141) was pumped into the reaction mass at a rate of about 1 g/minute aided by a vaporizer at 100° C. A total of 54 g of HCF-141 was fed over 55 minutes. During this time, the reactor was continuously vented at atmospheric pressure with the effluent continuously passed through a cold finger, cooled with solid $CO_2$ into a gas bulb then into a gas collection bag. 54 g of material was recovered.

GC analysis indicated 14% of the HCFC-141 had been converted to products. 71.7% of the product mixture was $CClF=CH_2$(HCFC=1131a); the rest was distributed among $CHF=CHCl$(HCFC-1131, both cis and trans), amounting to 25% of the product, $CClF=CClH$(HCFC-1121), 1.2%, and various saturated materials including $CH_3CF_3$(HFC-143a), $CHF_2CH_2F$(HFC-143), $CHFClCH_2F$(HCFC-142a), $CHF_2CH_2Cl$(HCFC-142), $CCl_2FCH_3$(HCFC-141b), $CHFClCH_2Cl$(HCFC-141), $CCl_2FCH_2Cl$(131a), $CHCl_2CHClF$(HCFC-131) and $CClF_2CCl_2F$(CFC-113).

The major product, $CClF=CH_2$, is an intermediate for preparing $CClF_2CH_3$(HCFC-142b), thence to $CF_2=CH_2$(CFC-1132a). Both HCFC-142b and CFC-1132a are industrially important and cannot be prepared directly from starting materials by halogen exchange processes. $CClF=CH_2$ is also an intermediate to $CF_3CH_2F$(HFC-134a) via $Cl_2$-addition and halogen exchange fluorination reactions in turn.

EXAMPLE 3

To a "Hastelloy" C Parr autoclave (600 cc) was added 757.5 g (5.0 mole) CsF and 99 g (1 mole) $CH_2ClCH_2Cl$(HCC-150). The autoclave was sealed, cooled to −78° C. and evacuated to a ca. 100 torr. Then 100.0 g (5 mole) HF was added, the reactor allowed to warm to room temperature and then heated to about 200° C. Time, temperature (190°–192° C.) and pressure were monitored and the reactor was sampled at 61 minutes (sample 1) 140 minutes (sample 2) and at shutdown at 180 minutes (sample 3). These data are shown below.

| Product | Sample 1 | Sample 2 | Sample 3 |
| --- | --- | --- | --- |
| $CH_2=CHF$ | 0.2% | 2.0% | 1.5% |
| $CH_2=CHCl$ | 1.9% | 41.0% | 3.4% |
| $CH_2FCH_2F$ | 92.5% | 42.1% | 92.6% |
| $CH_2FCH_2Cl$ | 4.7% | 8.5% | 2.3% |
| $CH_2ClCH_2Cl$ | 0.8% | 0.1% | 0.0% |
|  | 100.1% | 93.7% | 99.8% |

EXAMPLE 4

To a 600 cc Parr autoclave was added 759.5 g (5.0 mole) CsF and 90 g (4.5 mole) HF. Pot composition approximated CsF·0.9HF. After heating the reactor to 250° C., 2.85 moles $CH_2ClCH_2Cl$(HCC-150) were fed to the reactor at a rate of ca. 1 g/minute over 4.7 hours. The reactor effluent was condensed by means of a cold finger and collected continuously. Five samples were collected over the 4.7 hour run time. Results in terms of products formed follow:

| Sample # | Time (hrs) | Temp. (°C.) | $CH_2=CHF$ % | $FCH_2CH_2F$ % | $CH_2=CHCl$ % | $CH_2ClCH_2F$ % |
| --- | --- | --- | --- | --- | --- | --- |
| 1 | 0.42 | 252 | 0.244 | 3.208 | 5.376 | 1.588 |
| 2 | 1.60 | 251 | 0.266 | 1.766 | 5.708 | 0.977 |
| 3 | 2.70 | 251 | 0.298 | 1.272 | 3.463 | 0.411 |
| 4 | 3.72 | 251 | 0.232 | 0.570 | 1.129 | 0.265 |
| 5 | 4.72 | 250 | 0.385 | 0.603 | 1.090 | 0.282 |

EXAMPLE 5

To a 600 cc "Hastelloy" C autoclave was added 757.5 g (5 mole) CsF. The reactor was sealed and evacuated, then 100 g (5 mole) HF was added in one portion. The heat of reaction raised the reactor temperature to ca. 150° C. and the reactor was allowed to cool to room temperature (ca. 22° C.). To the reactor was then added 99 g (1 mole) HCC-150 in one portion and the system pressured up to 300 psig with dry nitrogen. The reactor was then warmed to 200° C. with a back pressure regulator set at 300 psig. Samples were collected periodically as pressures over 300 psig were vented by the back pressure regulator. The back pressure was reduced in steps to maintain sample collection. The samples were analyzed by GC and confirmed by GC/MS. Total run time was 15.5 hours. Results in terms of products formed follows:

| Sample # | Time (hrs) | Temp. (°C.) | Pressure (psig) | $CH_2=CHF$ % | $CH_2FCH_2F$ % | $CH_2=CHCl$ % | $CH_2FCH_2Cl$ % |
| --- | --- | --- | --- | --- | --- | --- | --- |
| 1 | 4.00 | 200 | 293 | 0.00 | 15.35 | 61.64 | 2.30 |
| 2 | 5.72 | 200 | 173 | 0.18 | 50.93 | 35.01 | 4.77 |
| 3 | 7.57 | 202 | 177 | 0.08 | 61.12 | 15.79 | 9.63 |
| 4 | 8.47 | 201 | 90 | 0.54 | 55.71 | 9.96 | 14.98 |
| 5 | 8.95 | 202 | 37 | 0.00 | 54.14 | 20.07 | 12.12 |
| 6 | 13.42 | 202 | 0 | 0.00 | 69.14 | 9.44 | 15.07 |

The haloolefins produced in Examples 3, 4 and 5, namely $CH_2=CHF$ and $CH_2=CHCl$, are used as intermediates to $CH_3-CHF_2$(HFC-152a) and $CH_3-CHClF$(HCFC-151a) through HF-addition reactions. These, in turn, are intermediates through chlorination reactions to $CH_3CClF_2$(HCFC-142b) and $CH_3CCl_2F$(HCFC-141b), all commercially useful.

EXAMPLE 6

To a 600 cc Parr autoclave was added 759.5 g (5 mole) CsF. The reactor was evacuated to vacuum and then 100 g (5 mole) HF was added. The reactor temperature increased due to the heat of reaction and then was cooled to below room temperature and 67.76 g (0.5 mole) $CHF_2CHCl_2$(HCFC-132a) was added. The reactor was then heated to ca. 200 C. while monitoring the temperature and pressure. Six samples were taken by venting the reactor through a heated line into a 5% KOH scrubber, then a gas bulb and then a dry test meter after 52(#1), 63(#2), 70(#3), 78(#4), 148(#5) and 156 minutes (#6). These were analyzed by GC and confirmed by GC/MS. Mass balance was 86%. The results follow:

| | | G. C. Analysis of Samples 1–6 | | | | | |
|---|---|---|---|---|---|---|---|
| F- | Product | 1 | 2 | 3 | 4 | 5 | 6 |
| 1123 | $CHF{=}CF_2$ | 0.16 | 0.21 | 0.19 | 0.17 | 0.05 | 0.05 |
| 134a | $CF_3CH_2F$ | 22.89 | 22.21 | 22.40 | 22.34 | 20.12 | 21.94 |
| 134 | $CHF_2CHF_2$ | 10.16 | 12.00 | 12.12 | 11.65 | 9.38 | 9.42 |
| 1122 | $CHCl{=}CF_2$ | 4.13 | 5.37 | 5.08 | 4.82 | 3.38 | 2.48 |
| 1122a | $CHF{=}CClF$ | 2.33 | 3.65 | 3.50 | 3.37 | 2.54 | 1.72 |
| 133a | $CF_3CH_2Cl$ | 22.76 | 26.83 | 26.94 | 26.43 | 27.90 | 22.30 |
| 133 | $CHClFCF_2$ | 1.21 | 2.24 | 2.17 | 2.15 | 2.23 | 1.45 |
| 1121a | $CHF{=}CCl_2$ | 6.46 | 10.24 | 10.98 | 11.33 | 14.25 | 13.42 |
| 132a | $CHF_2CHCl_2$ | 29.58 | 17.08 | 16.42 | 17.51 | 19.72 | 26.73 |

These data shows that haloolefins constitute up to about 25% of the reaction products.

All the haloolefins are convertible to $CF_3CH_2F$(HFC-134a) through HF-addition and halogen exchange reactions. They are also intermediates, via $Cl_2$-addition followed by halogen exchange fluorination, to $CHClFCF_3$(HCFC-124a) and $CHF_2CF_3$(HFC-125), which are also valuable low ozone depletion potential products.

What is claimed:

1. A process for preparing haloolefins containing a single double bond and at least one halogen substituent attached to an unsaturated carbon atom, which process comprises the following steps:
   (1) contacting component (A) a saturated halohydrocarbon having a hydrogen substituent and a halogen substituent on adjacent saturated carbon atoms and at least one other halogen substituent on at least one of the adjacent saturated carbon atoms with component (B) a substantially molten alkali metal acid fluoride or a molten mixture thereof with an alkali metal fluoride.

2. A process as in claim 1 wherein component (A) is selected from the group consisting of $CCl_2FCH_2Cl$, $CH_2ClCClF_2$, $CHClFCH_2Cl$, $CH_2ClCH_2Cl$ and $CHF_2CHCl_2$.

3. A process as in claim 1 wherein at least one haloolefin formed is selected from the group consisting of $CHF{=}CF_2$, $CHCl{=}CF_2$, $CHF{=}CClF$, $CHF{=}CCl_2$, $CH_2{=}CHF$, $CH_2{=}CHCl$, $CH_2{=}CClF$, $CHF{=}CHCl$ and $CClF{=}CHCl$.

4. A process as in claim 1 wherein said alkali metal acid fluoride and/or alkali metal fluoride are the fluorides of at least one of Cs, Rb and K.

5. A process as in claim 1 wherein component (B) contains molten cesium acid fluoride.

6. A process as in claim 1 wherein said temperature is about 150° C. to 500° C.

7. A process as in claim 1 wherein said pressure is from about atomspheric to about 30 atmospheres.

* * * * *